United States Patent
Kido et al.

[11] Patent Number: 5,897,546
[45] Date of Patent: Apr. 27, 1999

[54] DISPOSABLE DIAPER HAVING A FASTENING SYSTEM

[75] Inventors: Tsutomu Kido, Ehime-ken; Yoshihisa Fujioka, Kagawa-ken, both of Japan

[73] Assignee: Uni-Cham Corporation, Ehime-ken, Japan

[21] Appl. No.: 08/684,722

[22] Filed: Jul. 22, 1996

[30]     Foreign Application Priority Data

Aug. 2, 1995   [JP]   Japan .................................... 7-197731

[51] Int. Cl.⁶ .................................................. A61F 13/15
[52] U.S. Cl. ............................ 604/391; 604/386; 24/442
[58] Field of Search ............................. 604/385.1, 385.2, 604/386, 387, 389, 390, 391, 393, 394, 396; 24/442

[56]                References Cited

U.S. PATENT DOCUMENTS

| | | | |
|---|---|---|---|
| 3,638,651 | 2/1972 | Torr | 604/390 |
| 4,585,450 | 4/1986 | Rosch et al. | 604/390 |
| 4,662,875 | 5/1987 | Hirotsu et al. | |
| 4,810,574 | 3/1989 | Ahner | |
| 5,024,672 | 6/1991 | Widlund | 604/390 |
| 5,066,289 | 11/1991 | Polski | 604/390 |
| 5,531,731 | 7/1996 | Brusky | 604/390 |

FOREIGN PATENT DOCUMENTS

| | | |
|---|---|---|
| 0 532 805 | 9/1991 | European Pat. Off. . |
| 0 491 347 | 12/1991 | European Pat. Off. . |
| 7-22725 | 4/1995 | Japan . |
| 2267024 | 11/1993 | United Kingdom ................... 604/350 |
| WO92/01759 | 2/1992 | WIPO . |

*Primary Examiner*—Mark O. Polutta
*Attorney, Agent, or Firm*—Lowe Hauptman Gopstein Gilman & Berner

[57]                ABSTRACT

A disposable diaper has a fastening system comprising tape fasteners and a receiving sheet. The tape fasteners extend outward from transversely opposite side edges of a rear region 6 of the diaper. These tape fasteners are releasably fastened to the receiving sheet intermittently bonded by means of adhesive to an outer surface of a backsheet of the diaper. A color of the adhesive can be seen through the receiving sheet and serves as a positioning indicator when the tape fasteners are fastened to the receiving sheet.

7 Claims, 2 Drawing Sheets ated. 5,897,546

DISPOSABLE DIAPER HAVING A FASTENING SYSTEM

BACKGROUND OF THE INVENTION

The present invention relates to a disposable diaper having a fastening system for connecting a front waist and a rear waist of the diaper to each other.

Japanese Laid-Open Utility Model Application No. Hei7-22725 discloses a disposable diaper having tape fasteners extending outward from transversely opposite side edges of a rear region of the diaper adapted to be releasably fastened to receiving sheets bonded to an outer surface of a front region of the diaper, wherein graduations are marked on the receiving sheets in circumferentially around a waist of the diaper. These graduations serve as a positioning indicator when the tape fasteners are fastened to the receiving sheets so that these graduations may be utilized to maintain a tightening force around a wearer's waist at a constant level.

The receiving sheets are generally made of a plastic film or nonwoven fabric and the graduations are printed on surfaces of these receiving sheets. Particularly in the case of a baby diaper, materials used for the diaper should be carefully selected from the viewpoint of a sanitary security, since a baby often places their fingers or various other objects into their mouth. While hygienically innocuous ink is used for printing the graduations, it is desired to avoid contact between the ink and a baby's mouth.

Accordingly, it is a principal object of the invention to eliminate a demand of printing the graduation and to prevent regions occupied by the receiving sheets from becoming unacceptably rigid by utilizing a pattern in which an adhesive for bonding the receiving sheets to the front region is applied as the graduations.

SUMMARY OF THE INVENTION

The object set forth above is achieved, according to the invention, by a disposable diaper having a fastening system comprising tape fasteners extending outward from transversely opposite side edges of a rear region of the diaper, and a receiving sheet being bonded by means of adhesive to an outer surface of a front region of the diaper so that the tape fasteners may be releasably fastened to the receiving sheet. In the present invention adhesive is intermittently disposed circumferentially around a waist region of the diaper, the receiving sheet and the adhesive have relatively different colors, and the receiving sheet has a light transmissivity allowing the color of the adhesive to be seen through the receiving sheet.

DESCRIPTION OF THE PREFERRED EMBODIMENT

Figure 1:
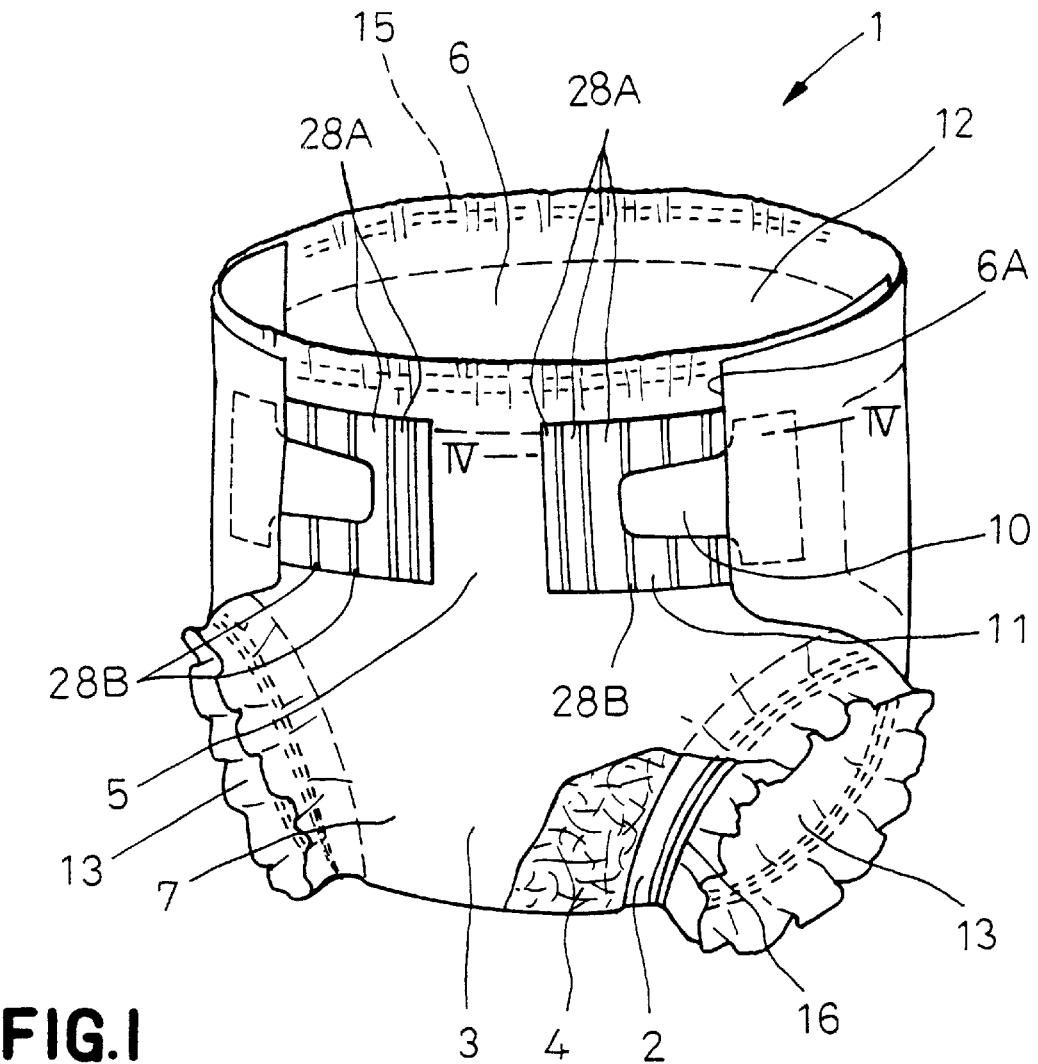
FIG. 1 is a perspective view showing a disposable diaper of the invention as partially broken away.

FIG. 1 is a partially broken away perspective view showing a diaper 1. As shown, the diaper 1 comprises a liquid-permeable topsheet 2, a liquid-impermeable backsheet 3 and a liquid-absorbent core 4 disposed between these two sheets 2, 3. The diaper 1 has a front region 5, a rear region 6 and a crotch region 7 longitudinally extending between these two regions 5, 6. Tape fasteners 10 laterally extend outward from transversely opposite edges 6A of the rear region 6, respectively, and are adapted to be releasably fastened to the front region 5 by engaging respective inner surfaces of these fasteners 10 with the receiving sheets 11 provided on an outer surface of the front region 5 at its transversely opposite edges. The diaper 1 is formed with a waist-opening 12 and a pair of leg-openings 13 by connecting of the front and rear regions 5, 6 are by means of the tape fasteners 10 to each other in such a manner as described above. The respective openings 12, 13 are circumferentially provided with elastically stretchable members 15, 16, respectively, which are bonded to at least one of respective inner surfaces of the topsheet 2 and the backsheets 3.

Figure 2:
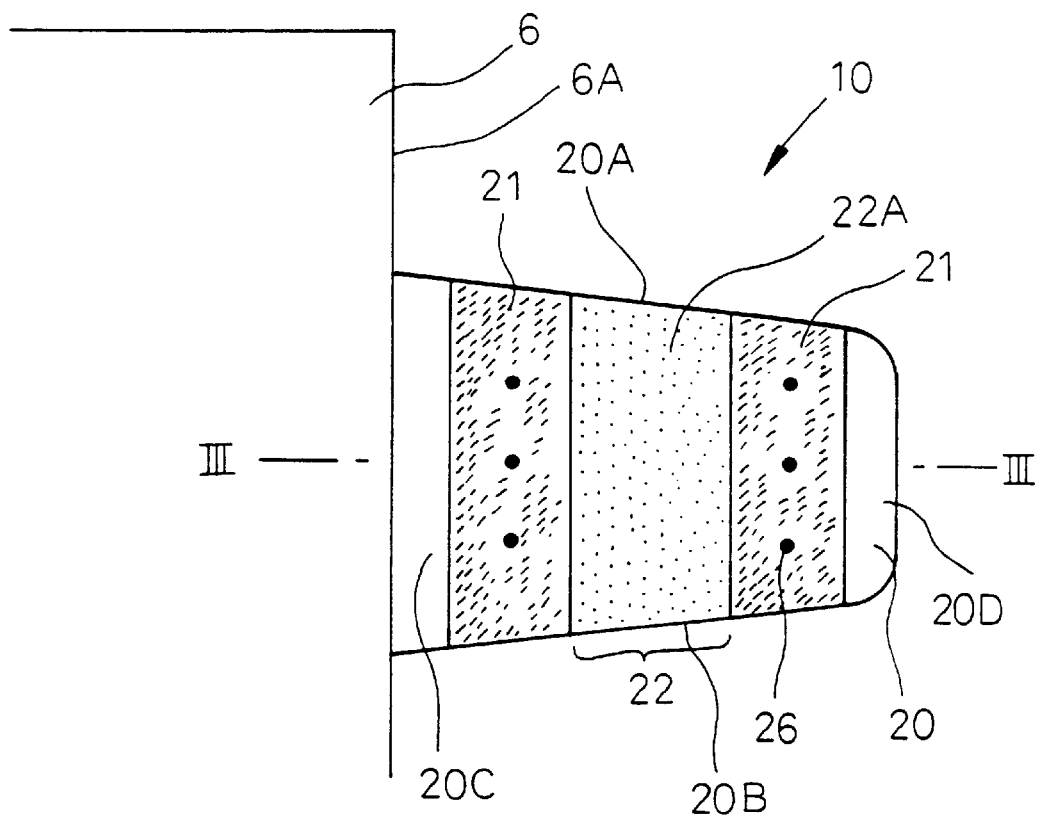
FIG. 2 is a plan view of a tape fastener.

The tape fastener 10 of which the inner side is depicted in FIG. 2 comprises a soft sheet member 20 formed of a nonwoven fabric made of thermoplastic synthetic fibers and fastening members 21 made of a plastic material having a rigidity higher than that of the sheet member 20. The fastening members 21 extend between upper and lower edges 20A, 20B of the sheet member 20 at locations spaced apart from each other, i.e., at a location adjacent a base end 20C and at a location adjacent a free end 20D with respect to the associated edge of the rear region 6 from which the tape fastener 10 laterally extends outward. The fastening members 21 are fixedly bonded to the sheet member 20 by means of an adhesive agent 22A and heat-sealing spots 26. The sheet member 20 is provided between the two fastening members 21 with an adhesive region 22 carrying the adhesive agent 22A exposed thereon. The free end 20D of the sheet member 20 is non-adhesive and serves as pick-up means.

Figure 3:
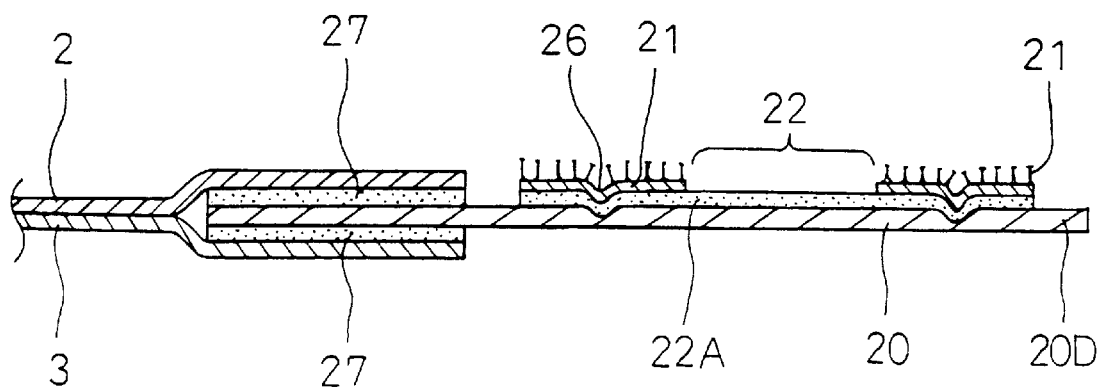
FIG. 3 is a sectional view taken along a line III—III in FIG. 2.

FIG. 3 is a sectional view taken along a line III—III in FIG. 2. As depicted, a part of the sheet member 20 is bonded to respective inner surfaces of the topsheet 2 and the backsheets 3. by means of hot melt adhesive 27. The paired fastening members 21 spaced apart from each other are bonded to an upper surface of the adhesive agent 22A and heat-sealed to the sheet member 20 by means of the heat-sealing spots 26. Each fastening member 21 corresponds to a plurality of hook elements of so-called surface fastener well known by the trade name of Velcro or Magic Tape and made of nylon or of plastic material. Each receiving sheet 11 to which the respective fastening members 21 are fastened comprises a bulky nonwoven fabric made of crimped fibers. The receiving sheet 11 has a color different from that of adhesive 30 depicted in FIG. 4 as will be described later and a light transmissivity allowing the color of the adhesive 30 to be seen therethrough. The receiving sheet 11 corresponds to a plurality of loop elements of the surface fastener. The receiving sheet 11 has a plurality of vertically extending stripes as seen in FIG. 1 so that each of these stripes may be used as a positioning indicator when the fastening members 21 are engaged with the respective receiving sheets 11.

Figure 4:
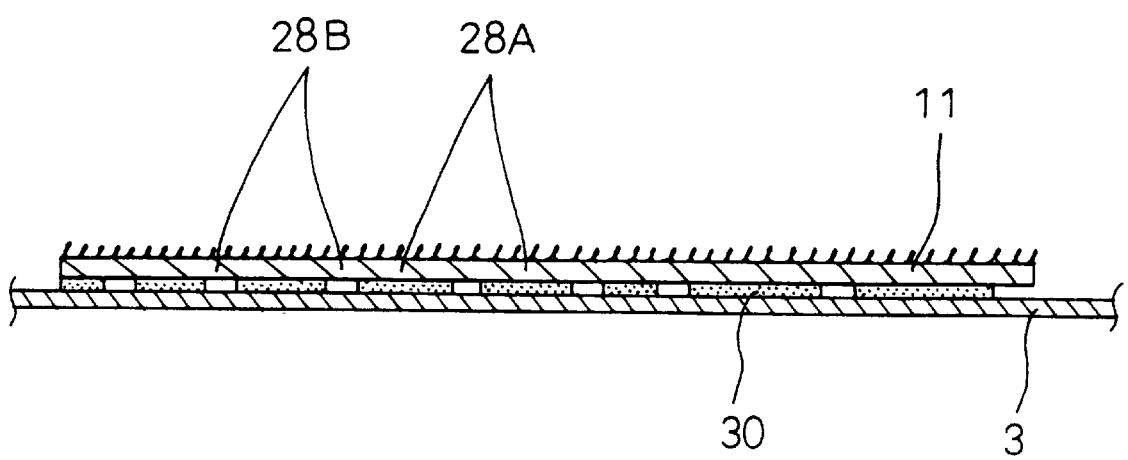
FIG. 4 is a sectional view taken along a line IV—IV in FIG. 1.

As will be apparent from FIG. 4 which is a sectional view taken along a line IV—IV in FIG. 1, the striped pattern is obtained by bonding the receiving sheet 11 to the backsheet 3 with use of colored hot melt adhesive 30 wherein the nonwoven fabric is applied with the colored hot melt adhesive 30 in the desired striped pattern. Referring to FIG. 4, sections 28A are bonded to the backsheet 3 and present a color of the hot melt adhesive therethrough while sections 28B are not bonded to the backsheet 3 and present a color of the receiving sheet itself. The pattern in which the receiving sheet 11 is applied with the hot melt adhesive and which serves as the positioning indicator may be selected from a group of appropriate patterns other than the striped pattern as adopted by the illustrated embodiment, so far as the adhesive is applied to the receiving sheet 11 intermittently along the waist line. Such intermittent application of adhesive may be performed over a limited extent predetermined for fastening of the member 21 and a peripheral region of the nonwoven fabric extending outside such predetermined extent may be, for example, continuously bonded to the backsheet 3. The pattern in which the adhesive 30 is applied and the shape of the sheet member 20 are preferably symmetric with respect to a transversely center line (not shown) of the diaper 1. To enhance the function of the adhesive application pattern as the indicator, the respective stripes may have widths progressively changing in the circumferential direction.

To implement the invention, a soft plastic film may be employed rather than the nonwoven fabric as a material for the sheet member 20 and an adhesive tape fastener may be employed rather than the fastening tape 21 as the tape fastener 10. The receiving sheet 11 associated with the adhesive tape fastener 10 is preferably made of a plastic film which must, obviously, allow the color of the hot melt adhesive to be seen therethrough. The receiving sheets 11 for both side edges of the front region 5 in the illustrated embodiment may be replaced by a single sheet which is continuous circumferentially around a wearer's waist. It should be understood that not only the adhesive agent such as hot melt adhesive but also the heat-sealing technique may be employed for bonding of the respective members, the latter being useful for the members made of a heat-sealable material.

In the diaper according to the invention, the receiving sheets 11 to which the tape fasteners 10 are fastened are intermittently bonded to the outer surface of the backsheet 3 and the bonded regions 28A thereof can be seen through the receiving sheets 11 so as to serve as the positioning graduations when the tape fasteners 10 are fastened to the respective receiving sheets 11. The adhesive 30 used for such bonding is covered with the receiving sheets and therefore reliably prevented from being in contact with a baby's hands and mouth, assuring a sanitary security of this diaper. According to the invention, application of the adhesive 30 makes printing of the graduations unnecessary and correspondingly allows the manufacturing cost to be reduced. Non-bonded regions 28B generated from intermittent application of the adhesive do not affect an air-permeability of the backsheet 3 and thus significantly improves an air-permeability of the diaper as a whole over the conventional case in which such receiving sheets 11 are bonded over the entire area thereof to the backsheet 3. Intermittent application of the adhesive 30 is advantageous also in that the regions occupied by the receiving sheets 11 do not present unacceptably a high rigidity and this advantageous effect is particular when the receiving sheets 11 are made of a nonwoven fabric.

What is claimed is:

1. An absorbent article and a fastening system therefor comprising:

said garment having a front region and a rear region, said garment including:

a liquid-permeable topsheet, a liquid-impermeable backsheet attached to said topsheet, a liquid-absorbent medium disposed between said topsheet and said backsheet;

tape fasteners extending outward from transversely opposite side edges of said rear region of the garment;

a receiving sheet being releasably fastened to said tape fasteners, said receiving sheet supporting a fastening material in the form of mechanical fasteners cooperating with said tape fasteners to secure the front and rear regions together; and an adhesive attached to said receiving sheet and bonded to said front region of said garment, wherein said adhesive is intermittently disposed along said receiving sheet to establish bonded regions and unbonded regions between said receiving sheet and said front region that form a visually observable pattern, said receiving sheet and said adhesive having relatively different colors, and said receiving sheet having a light transmissivity allowing the color of said adhesive to be seen through said receiving sheet in the bonded regions and not the unbonded regions.

2. The absorbent article as defined by claim 1, wherein said adhesive is disposed so as to form a pattern comprising a plurality of stripes extending vertically of the diaper.

3. The absorbent article and fastening system therefor as defined by claim 2, wherein said pattern of stripes is formed symmetrically about a center line which transversely divides said garment in two halves.

4. The absorbent article as defined by claim 1, wherein each of said tape fasteners comprises a plurality of hook elements.

5. The absorbent article as defined by claim 4, wherein said receiving sheet comprises a plurality of loop elements.

6. The absorbent article as defined claim 1, wherein each of said tape fasteners is made of adhesive tapes.

7. The absorbent article as defined claim 6, wherein said receiving sheet is made of a plastic film.

* * * * *